US00PP21441P2

(12) United States Plant Patent
Stemkens

(10) Patent No.: US PP21,441 P2
(45) Date of Patent: Nov. 2, 2010

(54) ***VERBENA* PLANT NAMED 'BLUDENA'**
(50) Latin Name: *Verbena×hybrida*
Varietal Denomination: Bludena

(75) Inventor: Henricus G. W. Stemkens, Andijk (NL)
(73) Assignee: Syngenta Crop Protection AG, Basel (CH)

( * ) Notice: Subject to any disclaimer, the term of this patent is extended or adjusted under 35 U.S.C. 154(b) by 0 days.
(21) Appl. No.: 12/586,704
(22) Filed: Sep. 25, 2009
(51) Int. Cl.
*A01H 5/00* (2006.01)

(52) U.S. Cl. ..... Plt./308
(58) Field of Classification Search ..... Plt./308
See application file for complete search history.

*Primary Examiner*—Susan B McCormick Ewoldt
(74) *Attorney, Agent, or Firm*—S. Matthew Edwards

(57) ABSTRACT

A new and distinct variety of *Verbena* plant named 'Bludena,' characterized particularly as to novelty by blue violet flowers, which appear earlier on the plant, and a growing habit that is first upright and later spreading.

1 Drawing Sheet

Latin name of the genus and species of the plant claimed: *Verbena×hybrida.*

Varietal denomination: 'Bludena'.

BACKGROUND OF THE NEW PLANT

The present invention comprises a new distinct cultivar of *Verbena*, botanically known as *Verbena×hybrida.*

The new *Verbena×hybrida* is a product of a planned breeding program conducted in Enkhuizen, Netherlands.

A new *Verbena* plant particularly distinguished by its blue-violet flowers, early flowering, and a growing habit that is first semi-erect and later spreading.

The new cultivar is propagated from cuttings resulting from the open pollination of 'G0503-5' and an unknown parent. 'G0503-5' is a bright rose flowering *Verbena* having a spreading habit. 'G0503-5' is not commercially available and is not known by any synonyms. The male parent is unknown. 'G0503-5' has not been patented. As a result of this open pollination the present cultivar was created in 2004 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

This new *Verbena* plant is an annual in most climatical zones in the US, only in zones 9 and 10 it is a perennial plant.

A Plant Breeder's Right for this cultivar was applied for in Europe on Nov. 12, 2008. 'Bludena' has not been made publicly available more than one year prior to the filing of this application.

DESCRIPTION OF THE DRAWING

This new *Verbena* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Verbena*. The data which defines these characteristics were collected from asexual reproductions carried out in Enkhuizen, Netherlands. The plant history was taken on 14 week old plants, blossomed under natural light in a greenhouse. Color readings were taken in the greenhouse under ambient light.

Color references are primarily to The R.H.S. Colour Chart of The Royal Horticultural Society of London.

TABLE 1

DIFFERENCES BETWEEN 'BLUDENA,' ITS PARENT, AND THE MOST RESEMBLING VARIETY

| | 'Bludena' | 'G0503-5' | 'Spikena' (U.S. Plant Pat. No. 12,452) |
|---|---|---|---|
| Flower color | N88A | Rose | 83A |
| Earliness | Early | Early | Late |
| Internode length | Short | Short | Long |
| Plant size | Compact | Compact | Big |

The plant:

*Classification botanical.*—*Verbena×hybrida.*

*Parentage.*—Female parent: 'G0503-5'. Pollen parent: Unknown.

*Growth habit.*—Semi-upright.

*Plant height.*—18-25 cm.

*Spreading area of plant.*—30-60 cm.

*Growth rate.*—Hanging and vigorous.

*Branching character.*—Freely branching and lateral branching at every node.

*Blooming period.*—From April until November.

The stem:

*Diameter.*—2.5-3 mm.

*Shape.*—Tetragonal.

*Anthocyanin pigmentation.*—Absent.

*Color.*—37B.

*Length of internode.*—18-32 mm, depending on the light where the plant is propagated.

*Pubescence.*—Pubescence is present.

The foliage:

*Phyllotaxis.*—Opposite.

*Shape of blade.*—Broadly ovate.

*Texture.*—Upper side: Pubescent. Lower side: Pubescent.

*Venation.*—Pinnate.

*Leaf margin.*—Sinuate.
*Leaf base.*—Shortly attenuate.
*Leaf apex.*—Abruptly acute.
*Length.*—25-35 mm.
*Width.*—18-25 mm.
*Depth of incision.*—0.5 mm.
*Color.*—Upper side: 137A. Lower side: 137C.
*Pubescence.*—Some pubescence is present.
*Length of leaf stem.*—2-3 mm.
*Petiole surface structure.*—Slightly pubescent.

The bud:

*Peduncle length.*—15-40 mm, depending on season.
*Size.*—Diameter: 2 mm. Length: 8-12 mm.
*Shape.*—Elongated and ovate.
*Color.*—137C.
*Sepals.*—Color: 138B. Form: Upright. Number: 5, fused. Size: 4.5 mm. Shape: Elongated.

The flower:

*Facing direction.*—Upward.
*Outward curvature of petal.*—Slightly curved.
*Diameter.*—20 mm.
*Height.*—18-20 mm.
*Borne.*—In a cluster.
*Form.*—Salverform; sessile on terminal spikes.
*Cluster.*—Spike.
*Color.*—N88A.
*Eye.*—No eye is present.
*Overlapping of petals.*—Separate.
*Number of petals.*—Gamopetalous, 5 lobed.
*Shape of the petals.*—Each petal is heart shaped at the apex and grown together at the base.
*Petal margin.*—Entire.
*Petal surface texture.*—Smooth.
*Size of the petal.*—Length: 6-8 mm. Width: 6-8 mm.
*Spike Length.*—25-35 mm. Diameter: 30-55 mm.
*Calyx length.*—8-10 mm.
*Anthocyanin pigmentation of calyx limb.*—Absent.
*Color of the calyx.*—137A.
*Number of flowers per spike.*—20-28.
*Fragrance.*—No fragrance.
*Lastingness of the bloom.*—New florets continue to open in one spike over a period of 14 days.
*Lastingness of one flower.*—5 days on the plant and 3 hours off the plant.

Reproductive organs:

*Androecium.*—Stamens quantity: 4. Anther shape: Ovoid. Anther length: 1 mm. Anther color: 144D. Pollen amount: Scarce pollen. Pollen color: 145D.
*Gynoecium.*—Pistils quantity: 1. Pistil length: 18-22 mm. Stigma shape: Bi-lobed. Stigma color: 144C. Style length: 14-18 mm. Style color: 144D. Ovary color: 144C.

No seed set is observed.

Physiological and ecological characteristics: Good tolerance to heat and cold, from 2-35 degrees C. No resistance to diseases common in *Verbena* is observed.

What is claimed is:

1. A new and distinct variety of *Verbena* plant named 'Bludena,' substantially as illustrated and described herein.

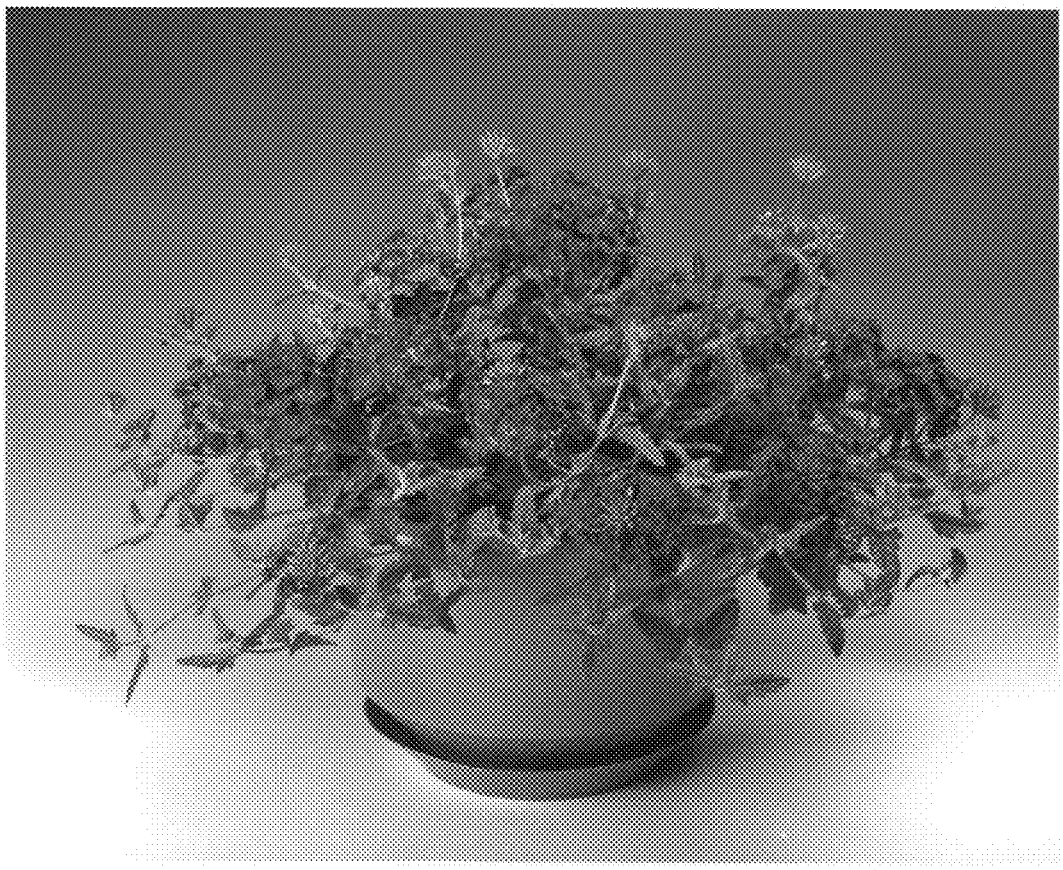

* * * * *